(12) United States Patent
Dan et al.

(10) Patent No.: US 11,985,971 B2
(45) Date of Patent: May 21, 2024

(54) ANTIBACTERIAL AND ANTIVIRAL COMPOSITION, AQUEOUS SOLUTION, SOAPS, SANITARY PRODUCT, HOUSE DETERGENT, KITCHEN DETERGENT, CLOTHING DETERGENT, ANTIBACTERIAL AND ANTIVIRAL AGENT FOR HOUSE, ANTIBACTERIAL AND ANTIVIRAL AGENT FOR KITCHEN, ANTIBACTERIAL AND ANTIVIRAL AGENT FOR CLOTHES, COSMETICS, WET WIPE, AND WET HAND TOWEL

(71) Applicant: VB JAPAN TECHNOLOGY CO., LTD., Kunitachi (JP)

(72) Inventors: Katsuaki Dan, Kashiwa (JP); Akiko Okayama, Tokyo (JP); Katsuyuki Fujinami, Tokyo (JP)

(73) Assignee: VB JAPAN TECHNOLOGY CO., LTD., Tokyo (JP)

( * ) Notice: Subject to any disclaimer, the term of this patent is extended or adjusted under 35 U.S.C. 154(b) by 0 days.

(21) Appl. No.: 17/041,032

(22) PCT Filed: Apr. 11, 2019

(86) PCT No.: PCT/JP2019/015791
§ 371 (c)(1),
(2) Date: Sep. 24, 2020

(87) PCT Pub. No.: WO2019/230210
PCT Pub. Date: Dec. 5, 2019

(65) Prior Publication Data
US 2021/0045382 A1   Feb. 18, 2021

(30) Foreign Application Priority Data
May 31, 2018   (JP) ................. 2018-104885

(51) Int. Cl.
| | | |
|---|---|---|
| A01N 25/34 | (2006.01) | |
| A01N 25/02 | (2006.01) | |
| A01N 47/44 | (2006.01) | |
| A01N 59/16 | (2006.01) | |
| A61K 8/19 | (2006.01) | |
| A61K 8/84 | (2006.01) | |
| A61P 31/04 | (2006.01) | |
| A61P 31/12 | (2006.01) | |

(52) U.S. Cl.
CPC ............ *A01N 25/34* (2013.01); *A01N 25/02* (2013.01); *A01N 47/44* (2013.01); *A01N 59/16* (2013.01); *A61K 8/19* (2013.01); *A61K 8/84* (2013.01); *A61P 31/04* (2018.01); *A61P 31/12* (2018.01)

(58) Field of Classification Search
CPC ........ A01N 25/34; A01N 25/02; A01N 59/16; A01N 47/44; A61K 8/19; A61K 8/84; A61K 31/29; A61K 33/24; A61P 31/04; A61P 31/12
See application file for complete search history.

(56) References Cited

U.S. PATENT DOCUMENTS

| | | | |
|---|---|---|---|
| 5,817,325 A | 10/1998 | Sawan et al. | |
| 5,849,311 A | 12/1998 | Sawan et al. | |
| 6,126,931 A | 10/2000 | Sawan et al. | |
| 6,264,936 B1 | 7/2001 | Sawan et al. | |
| 7,288,264 B1 | 10/2007 | Sawan et al. | |
| 8,802,132 B2 * | 8/2014 | Charest | A61L 15/46 424/442 |
| 9,487,912 B2 * | 11/2016 | Swamy | A01N 43/16 |
| 2005/0054546 A1 * | 3/2005 | Glick | C11D 3/3726 510/112 |
| 2014/0363520 A1 | 12/2014 | Dan et al. | |

FOREIGN PATENT DOCUMENTS

| | | | |
|---|---|---|---|
| EP | 1473047 B1 * | 10/2006 | ............. A61L 15/28 |
| JP | H08-73362 A | 3/1996 | |
| JP | H11-1630 A | 1/1999 | |
| JP | 2001-508041 A | 6/2001 | |
| JP | 2005-325083 A | 11/2005 | |
| JP | 2008-63271 A | 3/2008 | |
| JP | 2009-149575 A | 7/2009 | |
| JP | 2009-155262 A | 7/2009 | |
| JP | 2014-139164 A | 7/2014 | |
| JP | 2016-160245 A | 9/2016 | |
| JP | 2017-171606 A | 9/2017 | |
| JP | 2018-35280 A | 3/2018 | |
| JP | 2018-44077 A | 3/2018 | |
| SE | 1650162 A1 * | 8/2017 | ........... A61K 31/785 |
| WO | 1998/018330 A1 | 5/1998 | |
| WO | 2013/115062 A1 | 8/2013 | |

OTHER PUBLICATIONS

Varesano A, Vineis C, Aluigi A, and Rombaldoni F. "Antimicrobial polymers for textile products", Antimicrobial polymers for textile products. Science against microbial pathogens: communicating current research and technological advances. 2011; 3:99-110. (Year: 2011).*

Toshihiro Yamase, Norio Fukuda and Yutaka Tajima, "Synergistic Effect of Polyoxotungstates in Combination with B-Lactam Antibiotics on Antibacterial Activity against Methicillin-Resistant *Staphylococcus aureus*", Biological and Pharmaceutical Bulletin, 1996, 19(3), 459-465. (Year: 1996).*

Norio Fukuda and Toshihiro Yamase, "In Vitro Antibacterial Activity of Vanadate and Vanadyl Compounds against *Streptococcus pneumoniae*", Biological and Pharmaceutical Bulletin, 1997, 20(8), 927-930. (Year: 1997).*

(Continued)

*Primary Examiner* — John Pak
*Assistant Examiner* — Nathan W Schlientz
(74) *Attorney, Agent, or Firm* — Oliff PLC

(57) ABSTRACT

This antiviral and antibacterial composition includes: at least one of $VOSO_4$, $K_{11}H[(VO)_3(SbW_9O_{33})_2]$ and $Na_9[SbW_9O_{33}]$, and polyhexamethylene biguanide or a salt thereof.

14 Claims, 4 Drawing Sheets

(56) References Cited

OTHER PUBLICATIONS

Yamase T., Botar B., Ishikawa E., Fukaya K., Shigeta S. (2002) Magnetic Exchange Coupling and Potent Antiviral Activity of [(VO)3 (SbW9O33)2]12-. In: Yamase T., Pope M.T. (eds) Polyoxometalate Chemistry for Nano-Composite Design. Nanostructure Science and Technology. Springer, Boston, MA. (Year: 2002).*
Kelly R. Kirker, Steve T. Fisher, Garth A. James, Diane McGhee and Chirag B. Shah, "Efficacy of Polyhexamethylene Biguanide-containing Antimicrobial Foam Dressing Against MRSA Relative to Standard Foam Dressing", WOUNDS 2009, 21(9): 229-233. (Year: 2009).*
W. Fabry, C. Reimer, T. Azem, C. Aepinus, H.J. Kock and W. Vahlensieck, "Activity of the antiseptic polyhexanide against meticillin-susceptible and meticillin-resistant *Staphylococcus aureus*", Journal of Global Antimicrobial Resistance, 1, 2013, 195-199. (Year: 2013).*
W. Fabry and H.J. Kock, "In-vitro activity of polyhexanide alone and in combination with antibiotics against *Staphylococcus aureus*", Journal of Hospital Infection, 86, 2014, 68-72. (Year: 2014).*
Jul. 9, 2019 International Search Report issued in International Patent Application No. PCT/JP2019/015791.
Toshihiro Yamase. "Anti-Tumor, -Viral, and -Bacterial Activities of Polyoxometalates for Realizing an Inorganic Drug". Journal of Materials Chemistry, 2005, vol. 15, pp. 4773-4782.
Dec. 1, 2020 International Preliminary Report on Patentablitity issued in International Application No. PCT/JP2019/015791.
Mar. 3, 2021 Office Action issued in Chinese Patent Application No. 201980024021.8.
Yue, Rongxi et al., "Hospital Disinfection Technology and Application", People's Military Medical Press, Jan. 2013, p. 65.
Aug. 25, 2021 Office Action issued in Chinese Patent Application No. 201980024021.8.
Sao Shibasaki. "New Food Sterilization Technology", Agricultural Publishing House, Nov. 1990, p. 348.
Jan. 19, 2022 Office Action issued in Chinese Patent Application No. 201980024021.8.
Jun. 6, 2022 Office Action issued in Chinese Patent Application No. 201980024021.8.
Jan. 19, 2024 Office Action issued in Korean Patent Application No. 10-2020-7030062.

\* cited by examiner (a)

(b)

ANTIBACTERIAL AND ANTIVIRAL COMPOSITION, AQUEOUS SOLUTION, SOAPS, SANITARY PRODUCT, HOUSE DETERGENT, KITCHEN DETERGENT, CLOTHING DETERGENT, ANTIBACTERIAL AND ANTIVIRAL AGENT FOR HOUSE, ANTIBACTERIAL AND ANTIVIRAL AGENT FOR KITCHEN, ANTIBACTERIAL AND ANTIVIRAL AGENT FOR CLOTHES, COSMETICS, WET WIPE, AND WET HAND TOWEL

TECHNICAL FIELD

The present invention relates to an antibacterial and antiviral composition having antibacterial activity and antiviral activity, and an aqueous solution containing the antibacterial and antiviral composition.

BACKGROUND ART

In recent years, due to an increase in hygiene awareness, antibacterial substances have been contained in daily necessities and the like in order to improve sanitary conditions around kitchens and the like (for example, see Patent Literature 1). Further, antiviral substances having antiviral activity have been contained in daily necessities and the like in order to prevent infectious diseases such as influenza and the like (for example, see Patent Literature 2).

In addition, in a wet hand towel (Oshibori) such as a wet hand towel for rent based on a fiber product such as towel, or a disposable wet hand towel based on paper or nonwoven fabric, bacteria or viruses may attach to and grow, depending on an environment for use or storage of the wet hand towel. Therefore, hygiene management and preventive measures against infectious diseases are important issues also in a wet hand towel.

Although it is considered to use paraben or highly-concentrated alcohol against such bacteria or viruses, they may cause rough skin. Accordingly, Patent Literature 3 describes a disposable wet hand towel which has an antifungal effect with the use of an aqueous solution including ε-polylysine and an alkali metal salt of sorbic acid (for example, see Patent Literature 3).

Moreover, in cosmetics, antibacterial agents that are less irritating to the skin than parabens have been studied in order to prevent deterioration due to contamination of germs such as bacteria and mold during production and use (for example, see Patent Literature 4).

CITATION LIST

Patent Literature

Patent Literature 1: JP 2014-139164 A
Patent Literature 2: JP 2009-155262 A
Patent Literature 3: JP 2009-149575 A
Patent Literature 4: JP 2008-63271 A

SUMMARY OF INVENTION

Technical Problem

However, in Patent Literature 1, since there is a step of treating the antibacterial substance at a high temperature of 110 to 180° C. in order to make an aqueous solution, there has been a problem that the steps are complicated and the production cost is high. Further, in Patent Literature 2, since a suspension containing silica-containing particles or/and alumina-containing particles dispersed in water is used, stirring is required at the time of use, and it takes time to be used as an antiviral agent.

Furthermore, because the disposable wet hand towel of Patent Literature 3 may allow various kinds of bacteria and viruses to attach to and grow depending on environments for use and storage, it is desirable to have an antibacterial activity against various kinds of bacteria and an antiviral activity against various kinds of viruses.

In addition, a wet hand towel for rent is used in a rental destination such as a restaurant, showroom, office or beauty parlor, in which the wet hand towel is offered to a user. Further, after the wet hand towel for rent has been used, the wet hand towel will be recovered and washed, and then reused. In regards to the washing, the "Guideline for sanitary treatment of wet hand towel etc." from the Ministry of Health, Labor and Welfare requires that the number of bacteria after the washing should be equal to or less than the standard value.

However, a wet hand towel for rent is used in so various environments that various kinds of bacteria or viruses may attach to and propagate in the wet hand towel for rent. Therefore, it is required that a wet hand towel for rent has an antibacterial activity against not only a specific bacterium but also various kinds of bacteria, and an antiviral activity against not only a specific virus but also various kinds of viruses.

Further, antibacterial spectrum is not sufficient in the antibacterial agent of Patent Literature 4, and it is required that the antibacterial agent has an antibacterial activity against various kinds of bacteria.

Here, for the purpose of obtaining a composition which has an antibacterial activity against various kinds of bacteria and an antiviral activity against various kinds of viruses, it is considered that a plurality of compounds are combined, each of which has an antibacterial activity against a specific bacterium or an antiviral activity against a specific virus. However, when a plurality of compounds are randomly selected and combined, the combined compounds often react to each other or inhibit the antibacterial activity and antiviral activity of the compounds. Therefore, it has been difficult to obtain such a composition which has an antibacterial activity against various kinds of bacteria and an antiviral activity against various kinds of viruses.

An object of the present invention is to provide an antibacterial and antiviral composition which can be produced by a simple process, is easy to handle, and further has an antibacterial activity against various kinds of bacteria and an antiviral activity against various kinds of viruses, and an aqueous solution containing the composition.

Solution to Problem

As a result of earnest investigation, the present inventors have found that when a specific metal oxide cluster compound described in Literature 5 (Royal Society of Chemistry, Journal of Materials Chemistry, volume 15, pages 4773 to 4782, 2005) and a specific antibacterial agent are selected, the composition can be produced by a simple process and is easy to handle, and the compounds do not react with each other, and the antibacterial activity and antiviral activity of the compounds are not inhibited, and thus the present invention has been completed.

That is, according to the present invention, there are provided:
(1) an antibacterial and antiviral composition containing at least one of $VOSO_4$, $K_{11}H[(VO)_3(SbW_9O_{33})_2]$ and $Na_9[SbW_9O_{33}]$, and polyhexamethylene biguanide or a salt thereof, and
(2) an aqueous solution containing the antibacterial and antiviral composition according to (1).

DESCRIPTION OF EMBODIMENTS

Figure 1:
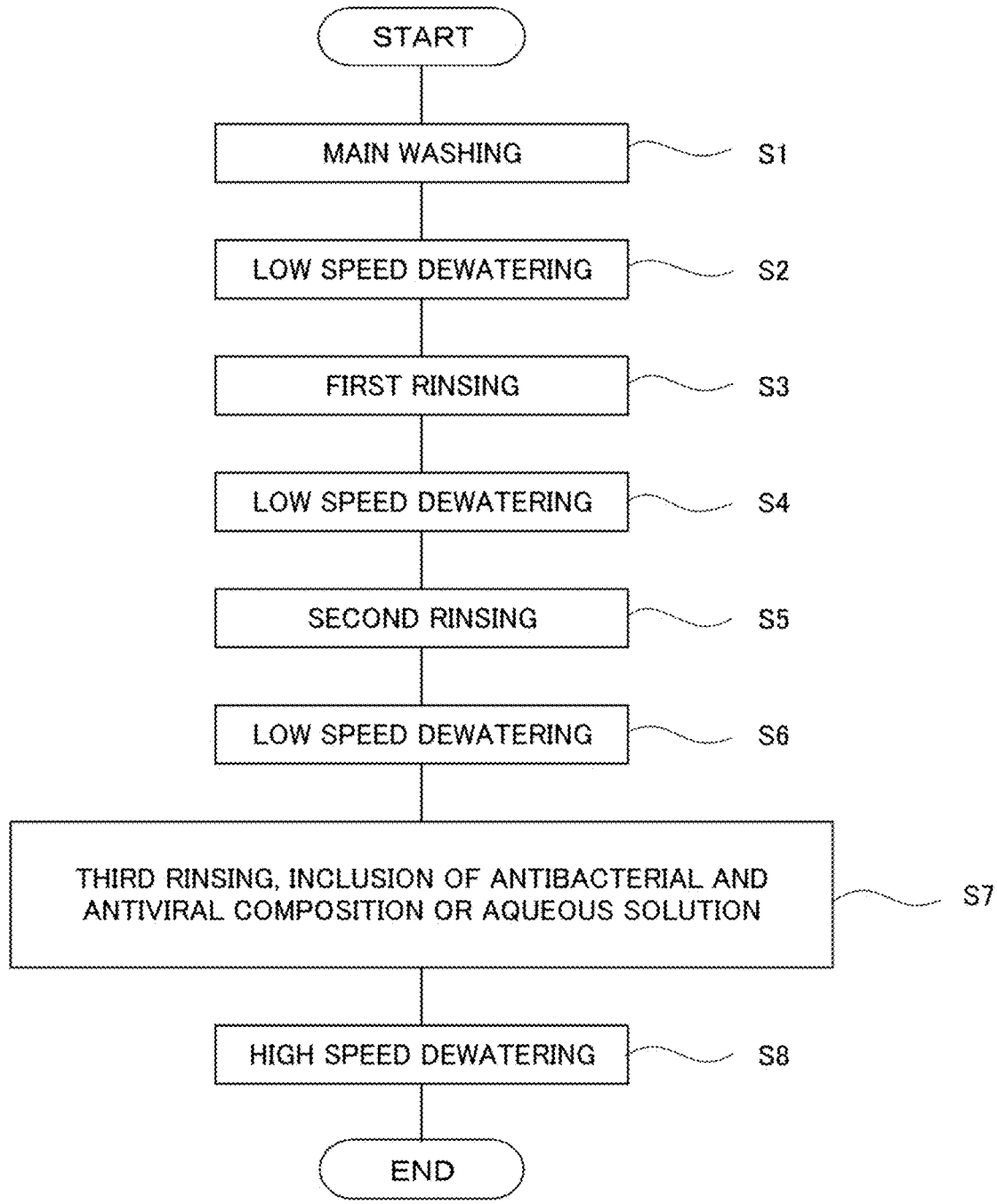
FIG. 1 is a flowchart that illustrates a process for producing a wet hand towel according to a first embodiment.

Hereinafter, the antibacterial and antiviral composition and aqueous solution of the present invention will be described. The antibacterial and antiviral composition of the present invention contains at least one of $VOSO_4$, $K_{11}H[(VO)_3(SbW_9O_{33})_2]$ and $Na_9[SbW_9O_{33}]$, and polyhexamethylene biguanide (hereinafter may be referred to as "PHMB") or a salt thereof, and the aqueous solution of the present invention contains the antibacterial and antiviral composition.

Here, the aqueous solution of the present invention is formulated from at least one of $VOSO_4$, $K_{11}H[(VO)_3(SbW_9O_{33})_2]$ and $Na_9[SbW_9O_{33}]$, and PHMB or a salt thereof at a predetermined ratio.

$VOSO_4$, $K_{11}H[(VO)_3(SbW_9O_{33})_2]$ and $Na_9[SbW_9O_{33}]$ are compounds belonging to a metal oxide cluster, called polyoxometalates (PM compounds). Here, the PM compounds are metal oxide cluster compounds having polyacid ions, and the compounds belonging to the PM compounds have their own biological activity such as an antibacterial activity and antiviral activity, as described in Literature 5 (Journal of Materials Chemistry, volume 15, pages 4773 to 4782, 2005, Royal Society of Chemistry). Note that, a poly acid means a metal oxide cluster compound constituted by a transition metal element (such as W(VI) and V(V)), which has a structure in which typically 4 or 6 oxygen atoms are coordinated to a metal atom or the like to form a tetrahedron or octahedron as a basic unit and the basic units are combined through their edges or peak points.

In addition, PHMB is a compound represented by formula (1).

{Chem. 1}

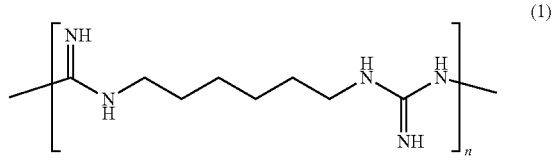

(1)

Wherein, in the formula (1), n represents an integer of 2 to 18, and n is preferably 12.

Further, PHMB is an odorless and less-irritating compound that is a safe compounded granule used as an industrial antibacterial agent in 30 countries around the world, and it is a compound that is hard to lose its effect because it is non-volatile. Furthermore, unlike hypochlorous acid and the like, it is a compound that does not corrode metals and rubbers, and thus can facilitate maintenance of factory facilities in the production process.

Note that, PHMB can be produced by a known method. Moreover, PHMB can also be used as a salt with hydrochloric acid, nitric acid, sulfuric acid, acetic acid or the like, and is preferably used as a hydrochloride in that it is easily available.

In addition, paragraph [0009] of JP 2018-35280 A and paragraph [0009] of JP 2016-160245 A describe that PHMB alone does not show a bactericidal effect on bacterial spores. Therefore, while it is considered impossible to predict whether or not a bactericidal effect on bacterial spores can be obtained even if the compound used with PHMB is arbitrarily selected, the antibacterial and antiviral composition and aqueous solution of the present invention have a bactericidal effect also on spores by using PHMB and the PM compound together.

Further, in the JP 2018-35280 A and JP 2016-160245 A above, in addition to adjust the pH of the composition containing PHMB to 12.5 or more, it is described that it is difficult to obtain an effect when the pH of the composition containing PHMB is not in the range of the alkaline region in paragraph [0027] of JP 2017-171606 A and paragraph [0014] of JP 2018-44077 A. However, the aqueous solution containing the antibacterial and antiviral composition of the present invention exerts its effect independently of pH by using PHMB and the PM compound together, unless it is extremely acidic and extremely alkaline.

The compounding ratio of the compound used in the present invention is not particularly limited, but $VOSO_4$ of preferably 0.1 to 20 M, further preferably 4 to 8 M, $Na_9[SbW_9O_{33}]$ of preferably 0.1 to 30 M, further preferably 10 to 20 M, and PHMB of preferably 0.1 to 30 M, further preferably 1 to 5 M are included, with respect to $K_{11}H[(VO)_3(SbW_9O_{33})_2]$ of 1 M.

In addition, it is particularly preferable that $VOSO_4$, $K_{11}H[(VO)_3(SbW_9O_{33})_2]$, $Na_9[SbW_9O_{33}]$ and PHMB be used at a molar ratio of 5.5:1:17.3:2.3.

When the antibacterial and antiviral composition of the present invention is dissolved in water for use as an aqueous solution, the aqueous solution is prepared such that the compounds which constitute the antibacterial and antiviral composition have a minimum effective concentration or higher. The compounds of $VOSO_4$, $K_{11}H[(VO)_3(SbW_9O_{33})_2]$, $Na_9[SbW_9O_{33}]$ and PHMB have the concentrations preferably in the aqueous solution of the present invention is from 1 to 50, from 10 to 300, from 50 to 1500, and from 1 to 100 μg/mL, respectively, further preferably from 20 to 40, from 50 to 150, from 500 to 1300, and from 5 to 15 μg/mL, respectively. In addition, the compounds of $VOSO_4$, $K_{11}H[(VO)_3(SbW_9O_{33})_2]$, $Na_9[SbW_9O_{33}]$ and PHMB which constitute the antibacterial and antiviral composition have concentrations in the aqueous solution of the present invention particularly preferably of 25, 115, 1000, and 10 μg/mL, respectively.

Further, the pH of the aqueous solution of the present invention is not particularly limited, but is preferably from 3 to 10, and more preferably from 4 to 9.

Here, the minimum inhibitory concentration (MIC) of the aqueous solution containing the antibacterial and antiviral composition of the present invention in which $VOSO_4$, $K_{11}H[(VO)_3(SbW_9O_{33})_2]$, $Na_9[SbW_9O_{33}]$ and PHMB are combined at a molar ratio of 5.5:1:17.3:2.3 is as shown in Table 1.

TABLE 1

| Classification | Type | MIC (ppm) |
| --- | --- | --- |
| Gram-positive bacteria | Staphylococcus aureus | 0.1 |
| | Streptococcus aureus | 10 |
| | Bacillus subtilis | 1 |
| Gram-negative bacteria | Escherichia coli | 3 |
| | Proteus Vulgaris | 1 |
| | Salmonella typhi | 1 |
| | Shigella dysenteriae | 3 |
| | Salmonella choleraesuis | 1 |
| Fungi | Trichophyton floccosum | 10 |
| | Epidermophyton floccosum | 10 |
| Mold | Peonicillium citrinum | 10 |
| | Candida albicans | 10 |

As shown in Table 1, even when the concentration of the antibacterial and antiviral composition contained in the aqueous solution of the present invention is low, the growth of microorganisms such as bacteria, fungi (molds) and viruses can be inhibited, and the antibacterial and antiviral composition and aqueous solution of the present invention have a broad antimicrobial spectrum. That is, the antibacterial and antiviral composition and aqueous solution of the present invention have activity against a wide variety of bacterial species. Furthermore, the antibacterial and antiviral composition and aqueous solution of the present invention also have activity against methicillin-resistant *Staphylococcus aureus* (MRSA). In addition, the aqueous solution containing the antibacterial and antiviral composition of the present invention is stable as an aqueous solution, and thus the long term storage is also possible.

Further, the antibacterial and antiviral composition of the present invention can maintain antibacterial and antiviral activities even at high temperatures up to 200° C., and is relatively stable even when temperature is raised. In addition, the compounds which constitute the antibacterial and antiviral composition of the present invention do not react with each other, and the antibacterial activity and antiviral activity of the compounds are not inhibited. Moreover, they are safe compounds so as not to cause rough skin and the like on the human body. Furthermore, the antibacterial and antiviral composition of the present invention is a safe compound that does not accumulate in the human body.

Further, the compounds contained in the antibacterial and antiviral composition and aqueous solution of the present invention are compounds that are not subject to environmental regulations, and the production process is not complicated, thus the production cost can be suppressed. In addition, in the antibacterial and antiviral composition and aqueous solution of the present invention, the effect is hardly reduced even when dirt is attached to a towel or the like as a substrate of a wet hand towel described later, and further, the effect is hardly reduced because of being non-volatile.

The antibacterial and antiviral composition and aqueous solution of the present invention may contain components such as other medical agents, moisturizing agents, and fragrances. Examples of the moisturizing agent include fulvic acid, hyaluronic acid, royal jelly, glycerin, soybean extract, and the like. Examples of the fragrance include is not particularly limited, but fragrance components having a fragrance such as citrus, peppermint, lavender, *Lindera umbellata*, *Magnolia salicifolia*, Japanese cypress, Japanese cedar, and fir, and an aroma oil and the like having such a fragrance can be used. The antibacterial and antiviral activities and antifungal performance of the antibacterial and antiviral composition and aqueous solution of the present invention are not inhibited by another medicinal solution, moisturizing agent or the like.

In addition, the antibacterial and antiviral composition of the present invention or an aqueous solution containing the composition may be contained in a known wet hand towel such as a paper wet hand towel, a nonwoven wet hand towel and a cloth wet hand towel, or may be contained in cosmetics such as skin lotion and milky lotion. Moreover, it may be contained in soaps such as hand soap, or may be contained in sanitary products such as masks and cotton swabs. Further, it may be contained in house detergents, kitchen detergents, clothing detergents, and the like, which are used in bathroom and bathtub, kitchen, tableware, clothes, and the like. Furthermore, the antibacterial and antiviral composition of the present invention may be contained in an exhaust filter for automobiles, or the antibacterial and antiviral composition of the present invention or an aqueous solution containing the composition may be contained in a filter for an air conditioner.

Also, the aqueous solution containing the antibacterial and antiviral composition of the present invention may be filled in a spray container and used as an antibacterial and antiviral agent for house, which is used in a floor or wall in a house or the like, and a fixture and furniture made of tiles, metal, plastic, glass, wood or the like in a house such as a table or the like installed in a house. Further, the aqueous solution containing the antibacterial and antiviral composition of the present invention may be filled in a spray container and used as an antibacterial and antiviral agent for kitchen, or an antibacterial and antiviral agent for clothes, which is used in bathroom and bathtub, kitchen, clothes, and the like. Moreover, the antibacterial and antiviral composition of the present invention or an aqueous solution containing the composition may be used as an antifungal agent. Note that, since the antibacterial and antiviral composition and aqueous solution of the present invention do not inhibit efficacy of components such as other medical agents, and the antibacterial and antiviral activities of the antibacterial and antiviral composition and aqueous solution of the present invention are not also inhibited by other medical agents or the like, as described above, other medical agents or the like may be contained in the antibacterial and antiviral composition and aqueous solution of the present invention.

Next, a case where the antibacterial and antiviral composition and aqueous solution of the present invention are applied to a wet hand towel will be described. When the antibacterial and antiviral composition and aqueous solution of the present invention are applied to a wet hand towel, for example, the antibacterial and antiviral composition or aqueous solution of the present invention can be contained in a substrate of the wet hand towel. Here, a towel, a nonwoven fabric, paper or the like can be used as the substrate of the wet hand towel. As a material of the towel, cotton or the like is used. In addition, a wet hand towel can be obtained by adding a predetermined amount or more of water to the substrate.

Hereinafter, a method for producing a wet hand towel according to a first embodiment of the present invention will be described. In the wet hand towel of the embodiment, a towel is mainly used as a substrate. In addition, the wet hand towel of the embodiment is a so-called wet hand towel for rent that is a towel used in a rental destination and then recovered after being used. Moreover, washing the wet hand towel according to the embodiment is performed so as to meet the "Guideline for sanitary treatment of wet hand towel etc." from the Ministry of Health, Labor and Welfare.

FIG. 1 is a flowchart that illustrates a process for producing a wet hand towel according to the first embodiment. A towel recovered after being used in a restaurant or the like is put into a cleaning tank of a washing machine, a detergent is put therein and main washing is performed (step S1), and low speed dewatering is performed for a predetermined time (step S2). Here, the main washing is performed at a predetermined temperature of 60° C. or more and a medium water level, for a predetermined time of 10 minutes or more.

Next, the cleaning tank is set to a high water level using clean water, first rinsing is performed at a predetermined temperature for a predetermined time (step S3), and low speed dewatering is performed for a predetermined time (step S4). Furthermore, the cleaning tank is set to the high water level using clean water, and also a bleaching powder or sodium hypochlorite is added so that free chlorine level reaches 250 ppm, second rinsing is performed at a predetermined temperature for a predetermined time (step S5), and low speed dewatering is performed for a predetermined time (step S6).

Thereafter, the cleaning tank is set to the middle water level using clean water, and also the antibacterial and antiviral composition or aqueous solution of the present invention is added thereto, and third rinsing is performed at a predetermined temperature for a predetermined time (step S7).

After the third rinsing has been completed, high speed dewatering is performed for a predetermined time (step S8). This step allows the towel to contain a predetermined amount of water, and the antibacterial and antiviral composition or aqueous solution of the present invention can be contained in the towel. In addition, after allowing the towel to contain the antibacterial and antiviral composition or aqueous solution of the present invention, the towel is formed into a predetermined shape to obtain a wet hand towel. Here, the towel can be formed into the predetermined shape by folding or winding the towel. In addition, after the towel is formed into the predetermined shape, the towel may be wrapped with a film or the like.

Wastewater containing the antibacterial and antiviral composition or aqueous solution of the present invention and the like discharged from the cleaning tank is collected in a treatment tank that performs wastewater treatment by a microbiological treatment method.

According to the first embodiment, it is possible to produce a wet hand towel having an antibacterial activity against various kinds of bacteria and an antiviral activity against various kinds of viruses. Further, an aqueous solution, not an organic solvent, is used, and the antibacterial and antiviral composition or aqueous solution of the present invention is used, thus it is also possible to prevent the effect on the human body such as rough skin.

In addition, a composition having an excellent antibacterial activity and an excellent antiviral activity can be contained in the wet hand towel at a low cost. Furthermore, the antibacterial and antiviral composition or aqueous solution of the present invention also has an antifungal effect, and a composition having an antifungal effect can be contained in the wet hand towel at a low cost. Moreover, the wastewater containing the antibacterial and antiviral composition or aqueous solution of the present invention does not have an adverse effect such as killing microorganisms (bacteria) in a treatment tank for performing a microbiological treatment method.

Figure 2:
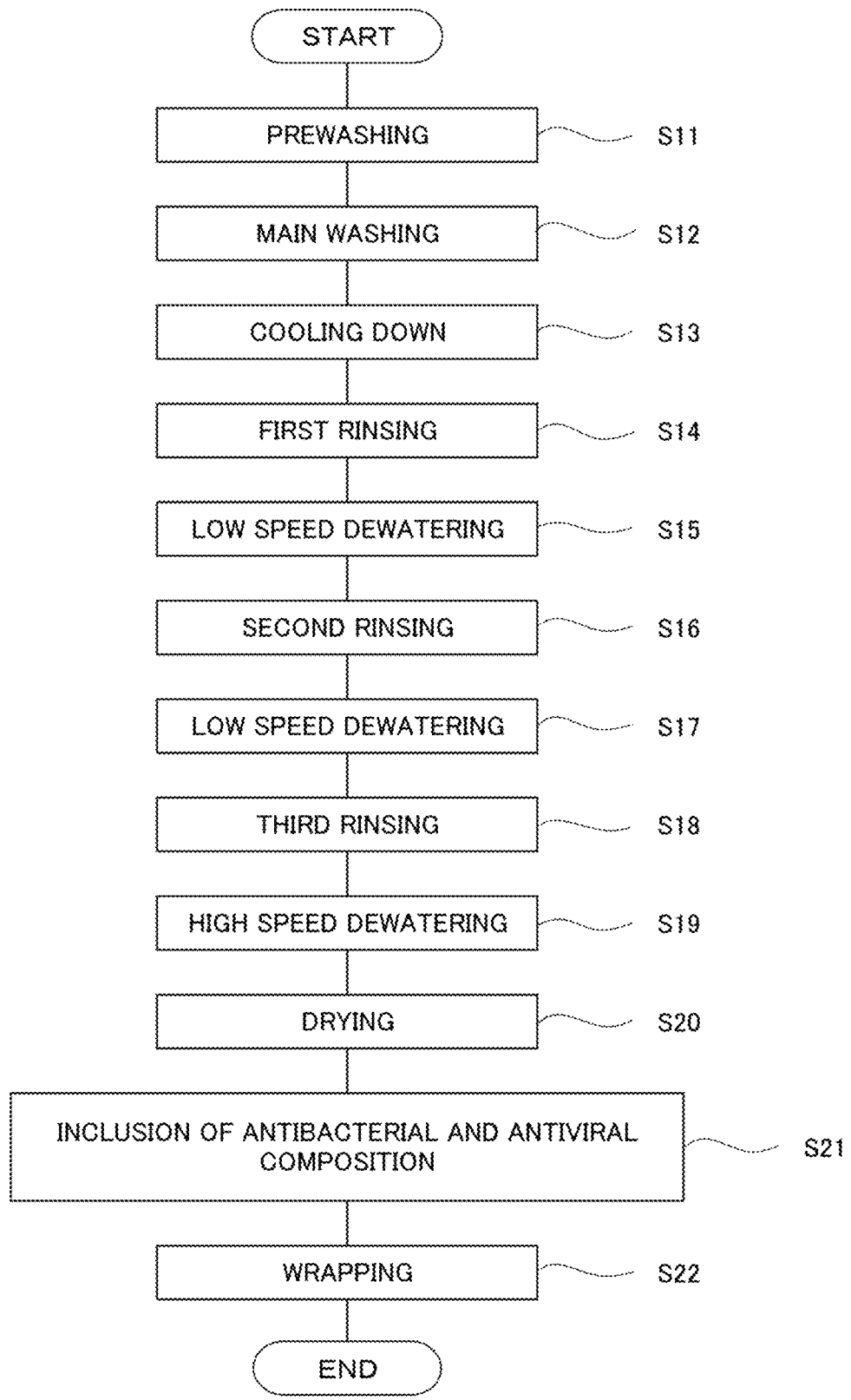
FIG. 2 is a flowchart that illustrates a process for producing a wet hand towel according to a second embodiment.
Figure 3:
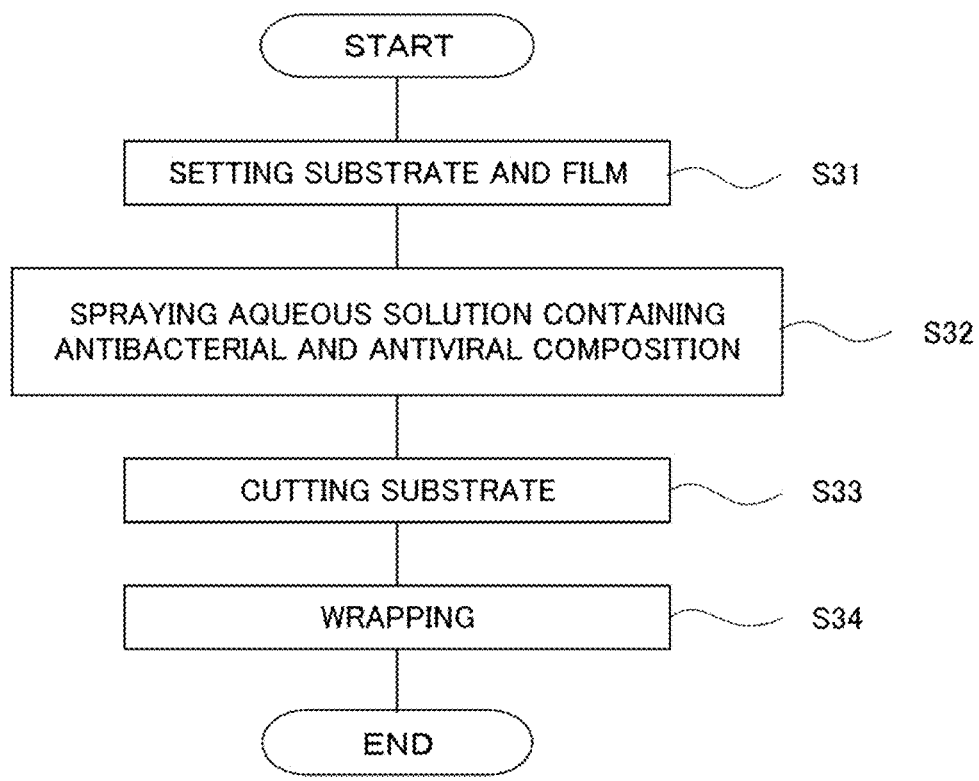
FIG. 3 is a flowchart that illustrates a process for producing a wet hand towel according to a third embodiment.

Note that, although in the method for producing a wet hand towel according to the first embodiment, the towel is configured to contain the antibacterial and antiviral composition or aqueous solution during the third rinsing, the antibacterial and antiviral composition or aqueous solution of the present invention may be contained in the towel during any of the steps as long as the towel can be configured to contain the antibacterial and antiviral composition or aqueous solution of the present invention. For example, the antibacterial and antiviral composition or aqueous solution of the present invention may be contained in a towel during the first rinsing or the second rinsing, or a towel may be immersed in the antibacterial and antiviral composition or aqueous solution of the present invention in a towel dipping tank after the high speed dewatering, as treatment shown in step S21 in FIG. 2 as described below, thereby immersing the antibacterial and antiviral composition or aqueous solution of the present invention in the towel. In addition, after forming a towel into a predetermined shape, the towel may be configured to contain the antibacterial and antiviral composition by being sprayed with the antibacterial and antiviral composition or aqueous solution of the present invention or the like.

Next, a method for producing a wet hand towel according to a second embodiment will be described. Note that, the method for producing a wet hand towel according to the second embodiment is changed to a configuration in which a new towel is used, instead of a recovered towel used as a substrate in the first embodiment. Therefore, a detailed description of the same configuration as that of the first embodiment will be omitted, and only a different part will be described in detail.

A new towel is put into a cleaning tank, and prewashing is performed at a predetermined temperature and a predetermined water level for several minutes without rotating the drum (step S1). Next, a desizing agent and a refining and penetrating agent are put therein, and main washing is performed at a predetermined temperature such as 80° C. and a predetermined water level for a predetermined time of 10 minutes or more (step S12), followed by cooling down at a predetermined temperature such as 60° C. for a predetermined time (step S13).

Then, rinsing and low speed dewatering are performed as shown in steps S14 to S17, in which the treatments are the same as those shown in steps S3 to 6 in the flow chart of FIG. 1, respectively, so the description thereof is omitted.

Thereafter, the cleaning tank is set to a predetermined water level using clean water, and also Niccanon (manufactured by Nicca Chemical Co., Ltd.) is added to reach 1 g/L, third rinsing is performed at a predetermined temperature for a predetermined time (step S18), and high speed dewatering is performed for a predetermined time (step S19).

Next, the towel that has undergone the high speed dewatering is taken out of the cleaning tank, and the towel is dried at 80° C. for a predetermined time in a drying machine (step 20). Thereafter, the antibacterial and antiviral composition of the present invention is contained in the towel (step S21). Here, the method for containing the antibacterial and antiviral composition of the present invention is not particularly limited, but a method for immersing a towel in an aqueous solution in which the antibacterial and antiviral composition of the present invention is dissolved, or a method for spraying a towel with the aqueous solution in which the antibacterial and antiviral composition of the present invention is dissolved.

When the towel is immersed, for example, clean water and the antibacterial and antiviral composition of the present invention are put in a towel dipping tank equipped with a stirring function, and stirred to obtain the aqueous solution in which the antibacterial and antiviral composition of the present invention is dissolved, and then the towel taken out of the cleaning tank is put in the towel dipping tank to be immersed. At this time, the compounds which constitute the antibacterial and antiviral composition of the present invention preferably have the concentrations in the aqueous solution preferably of several μg/mL or more.

In addition, the towel may be immersed with the use of a crane equipped with a jig for immersing a towel. Moreover, the towel may be immersed in the aqueous solution by attaching a buoyancy preventing weight attached to the towel. Next, after the aqueous solution has sufficiently infiltrated into the towel in the towel dipping tank, the towel is taken out of the towel dipping tank, lifted and left as it is until the aqueous solution drops from the towel. Thereafter, the towel is pressed using a press machine for several minutes.

Next, the towel that was allowed to contain the antibacterial and antiviral composition of the present invention is formed into a predetermined shape, and the towel is wrapped with a film using a wrapping machine (step S22), whereby it is possible to produce a wet hand towel according to the embodiment. Note that the moisture-vapor transmission rate of the film used in the embodiment is preferably equal to or lower than a predetermined value.

Wastewater containing the antibacterial and antiviral composition of the present invention and the like discharged from the cleaning tank is collected in a treatment tank that performs wastewater treatment by a microbiological treatment method.

According to the method for producing a wet hand towel according to the second embodiment, it is possible to produce a wet hand towel having an antibacterial activity against various kinds of bacteria and an antiviral activity against various kinds of viruses. Further, an aqueous solution, not an organic solvent, is used, and the antibacterial and antiviral composition or aqueous solution of the present invention is used, thus it is also possible to prevent the effect on the human body such as rough skin.

In addition, a composition having an excellent antibacterial activity and an excellent antiviral activity can be contained in the wet hand towel at a low cost. Furthermore, the antibacterial and antiviral composition and aqueous solution of the present invention also have an antifungal effect, and a composition having an antifungal effect can be contained in the wet hand towel at a low cost. Moreover, the wastewater containing the antibacterial and antiviral composition or aqueous solution of the present invention does not have an adverse effect such as killing microorganisms (bacteria) in a treatment tank for performing a microbiological treatment method.

Note that the washing machine for use in the above-described first and second embodiments is not particularly limited. A washing machine having one cleaning tank may be used, or a batch washing machine that individually performs prewashing, main washing, rinsing and the like in a single tank may be used, or a continuous washing machine that has a plurality of baths for prewashing, main washing, rinsing and the like in parallel and performs washing while moving an object to be washed such as a towel between the baths may be used.

In addition, the processes for producing the wet hand towel in the above-described first and second embodiments are only examples, and thus may be modified appropriately depending on the type or color of the substrate.

Next, a method for producing a wet hand towel according to a third embodiment will be described. Note that, the method for producing a wet hand towel according to the third embodiment is changed to a configuration in which paper, nonwoven fabric or the like is used, instead of the towel used in the first embodiment as a substrate.

First, a roll substrate made of paper or nonwoven fabric and a wrapping film are set on a wet hand towel producing machine (step S31). Next, the substrate is folded to a predetermined size by the wet hand towel producing machine, and an aqueous solution containing the antibacterial and antiviral composition of the present invention is sprayed to the folded substrate from above and below (step S32). Then, the substrate is cut into a predetermined size by a rotary blade provided in the wet hand towel producing machine (step S33), and the cut substrate is wrapped with the film (step S34), whereby it is possible to produce a wet hand towel of the embodiment.

According to the third embodiment, it is possible to produce a wet hand towel having an antibacterial activity against various kinds of bacteria and an antiviral activity against various kinds of viruses. Further, an aqueous solution, not an organic solvent, is used, and the aqueous solution containing the antibacterial and antiviral composition of the present invention is used, thus it is also possible to prevent the effect on the human body such as rough skin. In addition, a composition having an excellent antibacterial activity and an excellent antiviral activity can be contained in the wet hand towel at a low cost.

Further, in the third embodiment, since paper or nonwoven fabric is used as a substrate, it is possible to produce a disposable wet hand towel having an excellent antibacterial activity and excellent antiviral activity. Furthermore, the antibacterial and antiviral composition of the present invention also has an antifungal effect, and a composition having an antifungal effect can be contained in the wet hand towel at a low cost.

In addition, the wet hand towel produced through the method for producing a wet hand towel according to the third embodiment will satisfy the hygiene standard for a paper wet hand towel prescribed by Japan Cleansing Wipes Industry Association.

Note that, as the wet hand towel produced through the third embodiment, the substrate cut into a predetermined size in step S33 may be individually wrapped, or it may be so-called wet wipe in which a plurality of the substrates cut into a predetermined size in step S33 may be stored in a package such as a bottle so as to be taken out of this package one by one.

In order to be taken out one by one, it is preferable that the substrate is formed into a shape by a folding method or a winding method suitable for taking out one by one through an output port provided in the package.

In addition, although in each of the above-described embodiments, the wet hand towel is configured to contain the antibacterial and antiviral composition or aqueous solution of the present invention, components such as other medical agents may be further contained in the wet hand towel. In this case, for example, in the third embodiment, the aqueous solution containing the antibacterial and antiviral composition of the present invention is further added with another medicinal solution for wet hand towel, moisturizing agent or the like, and is sprayed. Examples of the moisturizing agent include fulvic acid, hyaluronic acid, royal jelly, glycerin, soybean extract, and the like. The antibacterial and antiviral composition or aqueous solution of the present invention does not inhibit efficacy of another medicinal solution for wet hand towel, moisturizing agent or the like, and the antibacterial and antiviral activities and antifungal performance of the antibacterial and antiviral composition and aqueous solution of the present invention are not inhibited by another medicinal solution for wet hand towel, moisturizing agent or the like.

Moreover, when the antibacterial and antiviral composition and aqueous solution of the present invention are applied to cosmetics, it is possible to produce cosmetics by mixing and stirring the antibacterial and antiviral composition or aqueous solution with any components selected from cosmetic raw materials such as water, alcohols, oils, moisturizing agents, whitening agents, UV inhibitors, anti-wrinkle agents, peeling agents, fragrances, coloring agents, surfactants, chelating agents, antioxidants, thickeners, and pH adjusters.

(manufactured by Nihon Pharmaceutical Co., Ltd.) was cultured at 35° C.±1° C. for 2 days by a pour plate culture method.

In addition, as a control, a 1/20 concentration of Nutrient Broth added with 0.1 mL of the test bacterial solution was inoculated into a standard cloth (cotton) for antibacterial test (Japan Textile Evaluation Technology Council) of the same size as above, and the test was performed in the same manner. The numbers of living bacteria at the starting time and 18 hours later were measured. The result is shown in Table 2. Note that, the measurement was performed three times for each of the aqueous solution containing the antibacterial and antiviral composition of the present invention and the control.

TABLE 2

| Test bacteria | Division | Test piece | Number of living bacteria per test piece | | |
|---|---|---|---|---|---|
| | | | Measurement-1 | Measurement-2 | Measurement-3 |
| MRSA | Immediately after inoculation | Specimen | $2.6 \times 10^4$ | $4.9 \times 10^4$ | $2.2 \times 10^4$ |
| | | Control | $5.3 \times 10^4$ | $4.3 \times 10^4$ | $5.8 \times 10^4$ |
| | after culture at 37° C. for 18 hours | Specimen | <20 | <20 | <20 |
| | | Control | $1.4 \times 10^7$ | $1.3 \times 10^7$ | $1.1 \times 10^7$ |

Bacterial solution prepared solution: 1/20 concentration nutrient medium
Control: Standard cloth (cotton) (Japan Textile Evaluation Technology Council)
<20: Not detected

EXAMPLES

Hereinafter, the present invention will be specifically described by showing Examples. However, the present invention is not limited to the following Examples, and can be arbitrarily changed to be performed within a range not departing from the gist of the invention and a scope equivalent thereto.

Example 1: Measurement of Antibacterial Activity Against MRSA

An aqueous solution containing the antibacterial and antiviral composition of the present invention ($VOSO_4$: 25 μg/mL, $K_{11}H[(VO)_3(SbW_9O_{33})_2]$: 115 μg/mL, $Na_9[SbW_9O_{33}]$: 1000 μg/mL, PHMB: 10 μg/mL) was diluted with a 1/20 concentration of Nutrient Broth, and 0.1 mL of a test bacterial solution was added to 10 mL of a specimen diluent (5000-fold diluted specimen) to produce a test solution. This test solution was inoculated into a standard cloth (cotton) for antibacterial test (Japan Textile Evaluation Technology Council) of a predetermined size, and the test was started.

Here, the test bacterial solution used was prepared such that test bacteria (Staphylococcus aureus, IID 1677 (MRSA)) had been cultured in Nutrient Agar (Difco) at 37° C. for 16 to 20 hours, and then suspended in the 1/20 concentration of Nutrient Broth (Difco) so as to have the number of bacteria of $10^6$ to $10^7$/mL.

The test solution was stored at 37° C., and each of the test solutions at the starting time (immediately after inoculation) and 18 hours later was immediately diluted 10 times on a medium for measuring the number of bacteria, and the measurement was performed using the number of living bacteria in the test solution. Note that, as the medium for measuring the number of bacteria, an SCDLP agar medium As shown in Table 2, an anti-MRSA effect of the antibacterial and antiviral composition and aqueous solution of the present invention was demonstrated such that the number of living bacteria of MRSA could be suppressed when the aqueous solution containing the antibacterial and antiviral composition of the present invention was used, as compared to when the aqueous solution containing the antibacterial and antiviral composition of the present invention was not used.

Example 2: Measurement of Antibacterial Activity Against Bacillus cereus

An aqueous solution containing the antibacterial and antiviral composition of the present invention ($VOSO_4$: 25 μg/mL, $K_{11}H[(VO)_3(SbW_9O_{33})_2]$: 115 μg/mL, $Na_9[SbW_9O_{33}]$: 10 0 0 μg/mL, PHMB: 10 μg/mL) was diluted with a 1/20 concentration of Nutrient Broth, and Bacillus cereus was added to 10 mL of a specimen diluent (5000-fold diluted specimen), then the obtained solution was inoculated into a standard cloth (cotton) for antibacterial test (Japan Textile Evaluation Technology Council) of a predetermined size. As Bacillus cereus, one bacterial strain of Bacillus cereus IFO13494 was used. Note that, in this measurement, an antibacterial activity test of the specimen was performed based on 10 quantitative test, 10.1 bacterial solution absorption method in JIS L 1902:2008 of "Testing for antibacterial activity and efficacy on textile products". In this antibacterial activity test, the specimen was not subjected to a high pressure steam sterilization (121° C., 15 minutes).

In addition, as a control, a 1/20 concentration of Nutrient Broth added with one bacterial strain of Bacillus cereus IFO13494 was inoculated into a standard cloth (cotton) for antibacterial test (Japan Textile Evaluation Technology Council) of the same size as above, and the test was performed in the same manner. The numbers of living bacteria at the starting time and 18 hours later were measured. The result is shown in Table 3.

In addition, a test using *Bacillus cereus* spores (*Bacillus cereus* IFO13494 (spores)) instead of *Bacillus cereus* was also performed in the same manner, and a control test was also performed in the same manner. The numbers of living bacteria in test pieces immediately after the inoculation of *Bacillus cereus* spores and after the culture for 18 hours were measured and shown in Table 3.

Figure 4:
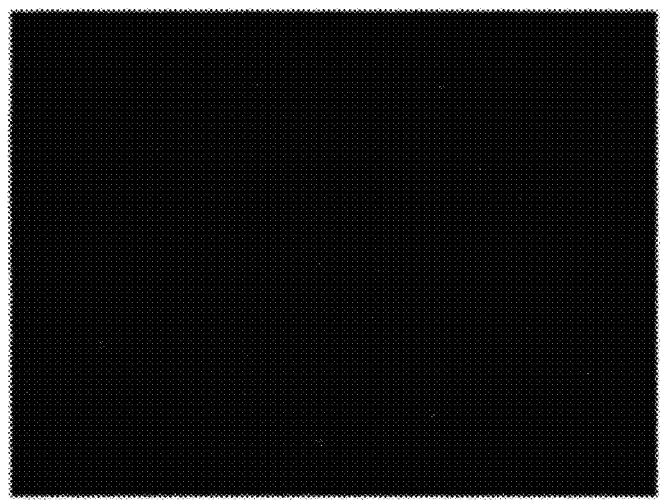
FIG. 4 shows images observed by a fluorescence microscope in the measurement of antiviral activity in Example 3.
Figure 4:
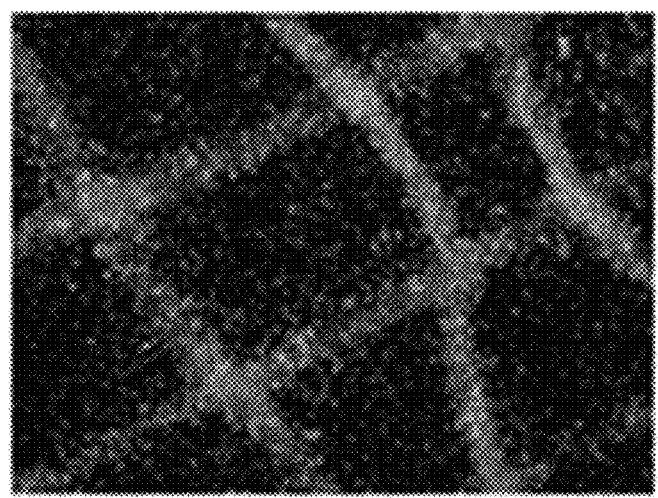

From the results shown in FIGS. 4(a) and 4(b), an anti-influenza virus effect of the antibacterial and antiviral composition and aqueous solution of the present invention was demonstrated such that almost no influenza virus was observed when the aqueous solution containing the antibacterial and antiviral composition of the present invention was used, as compared to when the aqueous solution containing

TABLE 3

| | | | Number of living bacteria per test piece | | |
|---|---|---|---|---|---|
| Test bacteria | Division | Test piece | Measurement-1 | Measurement-2 | Measurement-3 |
| *Bacillus cereus* | Immediately after inoculation | Specimen | $8.1 \times 10^2$ | $5.2 \times 10^2$ | $9.1 \times 10^2$ |
| | | Control | $2.4 \times 10^4$ | $2.1 \times 10^4$ | $2.2 \times 10^4$ |
| | after culture at 37° C. for 18 hours | Specimen | <20 | $1.4 \times 10^2$ | <20 |
| | | Control | $7.2 \times 10^6$ | $4.0 \times 10^6$ | $5.0 \times 10^6$ |
| *Bacillus cereus* (spores) | Immediately after inoculation | Specimen | $1.2 \times 10^5$ | $9.8 \times 10^4$ | $1.1 \times 10^5$ |
| | | Control | $8.6 \times 10^4$ | $1.1 \times 10^5$ | $9.2 \times 10^4$ |
| | after culture at 37° C. for 18 hours | Specimen | $2.1 \times 10^4$ | $3.3 \times 10^4$ | $2.0 \times 10^4$ |
| | | Control | $2.5 \times 10^6$ | $2.3 \times 10^6$ | $2.5 \times 10^6$ |

Bacterial solution prepared solution: 1/20 concentration nutrient medium
Control: Standard cloth (cotton) (Japan Textile Evaluation Technology Council)
<20: Not detected From the results shown in Table 3, an anti-*Bacillus cereus* effect of the antibacterial and antiviral composition and aqueous solution of the present invention was demonstrated such that the numbers of living bacteria of *Bacillus cereus* and *Bacillus cereus* (spores) could be suppressed when the aqueous solution containing the antibacterial and antiviral composition of the present invention was used, as compared to when the aqueous solution containing the antibacterial and antiviral composition of the present invention was not used.

Example 3: Measurement of Antiviral Activity Against Influenza Virus

An aqueous solution containing the antibacterial and antiviral composition of the present invention (VOSO$_4$: 25 µg/mL, K$_{11}$H[(VO)$_3$(SbW$_9$O$_{33}$)$_2$]: 115 µg/mL, Na$_9$[SbW$_9$O$_{33}$]: 1000 µg/mL, PHMB: 10 µg/mL) was diluted with a 1/20 concentration of Nutrient Broth, and a standard cloth (cotton) for antibacterial test (Japan Textile Evaluation Technology Council) of a predetermined size was added to a specimen diluent (5000-fold diluted specimen) to obtain a test specimen. Next, this test specimen was immersed in a solution of influenza virus at 37° C. for 5 minutes. Then, a test specimen was taken out of the influenza virus solution and immersed in an antiviral solution. After taking out the test specimen from the antiviral solution, the specimen was treated with a fluorescently labeled virus antibody, and observed with a fluorescence microscope. The result of observation with a fluorescence microscope is shown in FIG. 4(a). In addition, a control experiment was performed in the same procedure except that water was used instead of the aqueous solution containing the antibacterial and antiviral composition of the present invention. The result of observation with a fluorescence microscope in the control experiment is shown in FIG. 4(b). Note that, in FIGS. 4(a) and 4(b), portions that are not blackened are areas where fluorescence is observed, indicating that the influenza virus is present in the areas where fluorescence is observed.

the antibacterial and antiviral composition of the present invention was not used.

The invention claimed is:

1. An aqueous solution comprising an antibacterial and antiviral composition containing VOSO$_4$, K$_{11}$H[(VO)$_3$(SbW$_9$O$_{33}$)$_2$], Na$_9$[SbW$_9$O$_{33}$], and polyhexamethylene biguanide as the only compounds having antibacterial or antiviral activity in the antibacterial and antiviral composition,
wherein in the antibacterial and antiviral composition:
the compounding ratio of VOSO$_4$ is 0.1 to 20 M,
the compounding ratio of Na$_9$[SbW$_9$O$_{33}$] is 0.1 to 30 M, and
the compounding ratio of polyhexamethylene biguanide is 0.1 to 30 M, with respect to 1 M of K$_{11}$H[(VO)$_3$(SbW$_9$O$_{33}$)$_2$], and
wherein the aqueous solution comprises:
1 to 50 µg/mL VOSO$_4$,
10 to 300 µg/mL K$_{11}$H[(VO)$_3$(SbW$_9$O$_{33}$)$_2$],
50 to 1500 µg/mL Na$_9$[SbW$_9$O$_{33}$], and
1 to 100 µg/mL polyhexamethylene biguanide.

2. The aqueous solution according to claim 1, having a pH in the range of from 3 to 10.

3. The aqueous solution according to claim 1, comprising: the VOSO$_4$, K$_{11}$H[(VO)$_3$(SbW$_9$O$_{33}$)$_2$], Na$_9$[SbW$_9$O$_{33}$], and polyhexamethylene biguanide in a molar ratio of 5.5:1:17.3:2.3.

4. The aqueous solution according to claim 1, comprising:
20 to 40 µg/mL VOSO$_4$,
50 to 150 µg/mL K$_{11}$H[(VO)$_3$(SbW$_9$O$_{33}$)$_2$],
500 to 1300 µg/mL Na$_9$[SbW$_9$O$_{33}$], and
5 to 15 µg/mL polyhexamethylene biguanide.

5. The aqueous solution according to claim 1, wherein the concentrations of VOSO$_4$, K$_{11}$H[(VO)$_3$(SbW$_9$O$_{33}$)$_2$], and Na$_9$[SbW$_9$O$_{33}$], and polyhexamethylene biguanide in the aqueous solution are effective to prevent an effect on a human body.

6. The aqueous solution according to claim 1, wherein the concentrations of $VOSO_4$, $K_{11}H[(VO)_3(SbW_9O_{33})_2]$, and $Na_9[SbW_9O_{33}]$, and polyhexamethylene biguanide in the aqueous solution are effective to provide antibacterial or antiviral effects on human skin without increasing roughness of the skin.

7. Soaps comprising the aqueous solution according to claim 1.

8. A sanitary product comprising the aqueous solution according to claim 1.

9. A house detergent comprising the aqueous solution according to claim 1.

10. A kitchen detergent comprising the aqueous solution according to claim 1.

11. A clothing detergent comprising the aqueous solution according to claim 1.

12. Cosmetics comprising the aqueous solution and antiviral composition according to claim 1.

13. A wet wipe comprising the aqueous solution according to claim 1.

14. A wet hand towel comprising the aqueous solution according to claim 1.

* * * * *